US006492168B1

(12) United States Patent
Kladde et al.

(10) Patent No.: US 6,492,168 B1
(45) Date of Patent: Dec. 10, 2002

(54) METHYLTRANSFERASE GENE AND ENZYME

(75) Inventors: Michael P. Kladde, Bryan, TX (US); Robert T. Simpson, Lemont, PA (US); Mai Xu, Hangzhou (CN)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/296,840

(22) Filed: Apr. 22, 1999

Related U.S. Application Data

(60) Provisional application No. 60/082,674, filed on Apr. 22, 1998.

(51) Int. Cl.[7] .......................... C12N 5/00; C12N 15/00; C12N 15/63; C07H 21/02; C07H 21/04
(52) U.S. Cl. .................... 435/325; 435/320.1; 435/455; 435/468; 435/471; 435/252.3; 435/254.1; 435/410; 536/23.1; 536/23.2; 536/23.72; 536/24.33
(58) Field of Search .................... 435/183, 193, 435/235.1, 320.1, 325, 455, 468, 471, 252.3, 254.1, 410; 536/23.1, 23.2, 23.7, 23.72, 24.33

(56) References Cited

PUBLICATIONS

Kimmel, Guide to Molecular Cloning Techniques, 1987, vol. 152, pp. 673–695.*
Kayle, A single amino acid substitution results in a retinoblastoma protein defective in phosphorylation and oncoprotein binding, Sep. 1990, Proc. Natl. Acad. Sci., vol. 87, pp. 6922–6926.*
Shichijo et al., Detection of Mage–4 Protein in Lung Cancers, 1995, Int. J. Cancer, vol. 64, pp. 158–165.*
Rudinger et al., Characteristics of the amino acids as components of a peptide hormone sequence, Jun. 1976, pp. 1–7.*
Bussey,H., et al. The nucleotide sequence of chromosome I from *Saccharomyces cerevisiae*. *Proc. Natl Acad. Sci. USA.* 1995 92:3809–3813.
Cheng,X., et al. Crystal Structure of the HhaI DNA Methyltransferase Complexed with S–Adenosyl–l–Methionine. *Cell.* 1993 74:299–307.
Dujon,B., et al. Complete DNA sequence of yeast chromosome XI. *Nature.* 1994 369:371–378.
Jacq,C., et al. The nucleotide sequence of *Saccharomyces cerevisiae* chromosome IV. *Nature.* 1997 387 (suppl. 6632): 75–78.

Kladde,M.P., Xu,M. and Simpson,R.T. Direct study of DNA–protein interactions in repressed and active chromatin in living cells. *EMBO J.* 1996 15:6290–6300.
Kumar, S. et al. The DNA (cytosine–5) methyltransferases. *Nucl. Acids Res.* 1993 22:1–10.
Nelson,M., Burbank,D.E. and Van Etten,J.L. Chlorella Viruses Encode Multiple DNA. *Biological Chem.* 1998 379: 423–428.
Nelson,M., Zhang,Y. and Van Etten,J.L. DNA methyltransferases and DNA site–specific endonucleases encoded by chlorella viruses. *DNA Methylation: Molecular Biology and Biological Significance.* 1993 Birkhauser–Verlag Press, Basel, Switzerland:186–211.
Posfai,J., et al. Predictive motifs derived from cytosine methyltransferases. *Nucleic Acids Res.* 1989 17:2421–2435.
Raleigh,E.A. [12] Restriction and Modification in Vivo by *Escherichia coli* K12. *Methods Enzymol.* 1987 152:130–141.
Reinisch,K.M., et al. The Crystal Structure of HaeIII Methyltransferase Covalently Complexed to DNA: An Extrahelical Cytosine and Rearranged Base Pairing. *Cell.* 1995 82:143–153.
Renbaum,P., et al. Cloning, Characterization, and expression in *Escherichia coli* of the gene coding for the CpG DNA methylase from spiroplasma sp strain MA1 (M•SssI). *Nucleic Acids Res.* 1990 18:1145–1152.
Schuster,A.M., et al. Characterization of Viruses Infecting a Eukaryotic Chlorella–like Green Alga. *Virology* 1986 150:170–177.
Shields,S.L., et al. Cloning and Sequencing the Cytosine Methyltransferase Gene M.CviJl from Chlorella Virus IL–3A *Virology* 1990 176:16–24.
Tazi,J. and Bird,A. Alternative Chromatin Structure at CpG Islands *Cell* 1990 60:909–920.
Zhang,Y., Nelson,M. and Van Etten,J.L. A single amino acid change restores DNA cytosine methyltransferase activity in a cloned chlorella virus pseudogene *Nucleic Acids Res* 1992 20:1637–1642.

* cited by examiner

*Primary Examiner*—Scott D. Priebe
*Assistant Examiner*—Shin-Lin Chen
(74) *Attorney, Agent, or Firm*—McKee, Voorhees & Sease, P.L.C.

(57) ABSTRACT

A novel cytosine-5 DNA methyltransferase, isolated from Chlorella virus NYs-1, and its encoded enzyme are disclosed. The methyltransferase recognizes a GpC dinucleotide in DNA. Methods of using the novel methyltransferase in high resolution chromatin mapping and related techniques are also disclosed.

16 Claims, 4 Drawing Sheets

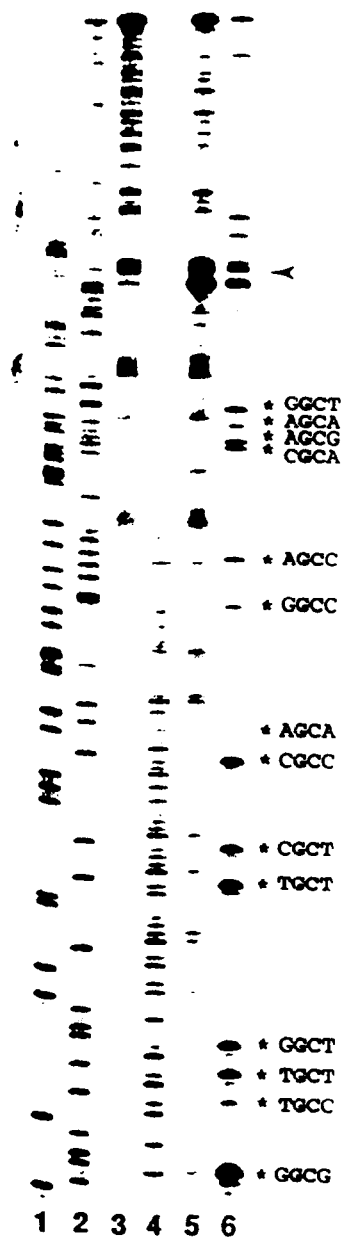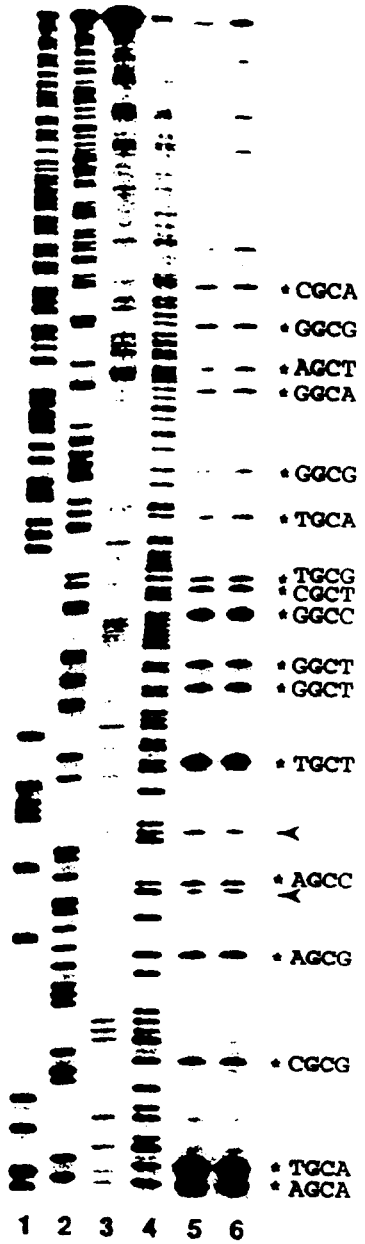
Figure 1

```
                           I
M.CviPI    1  MTLKALELFAGIAGITHGLRGFVEPVAFV.EINKDAQEFLSTKFPDKPVFDDVTKFSKRDFDEPI
M.CviJI    1  MSFRTLELFAGIAGISHGLRGISTPVAFV.EINEDAQKFLKTKFSDASVFNDVTKFTKSDFPEDI
M.HaeIII   1  MNL..ISLFSGAGGLDLGFQKAGFRIICANEYDKSIWKTYESNHSAKLIKGDISKISSDEFPK.C
                    IV                          VI
M.CviPI   65  DMITGGFPCTGFSIAGKRNGFEHAESGLFGEVVRITKEYMPKMVFLENS.GMLS..HKYNLDIVI
M.CviJI   65  DMITAGFPCTGFSIAGSRTGFEHKESGLFADVVRITEEYKPKIVFLENS.HMLS..HTYNLDVVV
M.HaeIII  63  DGIIGGPPCQSWSEGGSLRGIDDPRGKLFYEYIRILKQKKPIFFLAENVKGMMAQRHNKAVQEFI

VIII
M.CviPI  127  RSMDSLGYDCRWVTLRATVVGALHTRHRWFCLCTRKDHIRETLICDREVTKFDWENDRPPIQVDS
M.CviJI  127  KKMDEIGYFCKWVTCRASIIGAHHQRHRWFCLAIRKDYEPEEIIVSVNATKFDWENNEPPCQVDN
M.HaeIII 128  QEFDNAGYDVHIILLNANDYGVAQDRKRVFYIGFRKELN.......INYLPPIPHLIKPTFKDVI

_ _ TRD _  _
M.CviPI  192  RSYENSRLVRFAGYSVVPDQIRYAFTGLYTGNFSPSFSKTLVPGSLEG....SICFNEDKITNGY
M.CviJI  192  KSYENSTLVRLAGYSVVPDQIRYAFTGLFTGDFESSWKTTLTPGTIIGTEHKKMKGTYDKVINGY
M.HaeIII 186  WDLKDNPIPALDKNKTNGNKCIYPNHEYFIG....SYSTIFMSRNRVR......QWNEPAFT...

M.CviPI  253  YKDGVYYEFVRTETH.REPVNILLTPREIPNKHNGKKLLTLPVTKRYWCTPCASYGKGTAGGRVL
M.CviJI  257  YENDVYYSFSRKEVH.RAPLNISVKPRDIPEKHNGKTLVDREMIKKYWCTPCASYGTATAGCNVL
M.HaeIII 237  ....VQASGRQCQLHPQAPVMLKVS.KNLNKFVEGKEHLYRRLTVR....ECAR....VQG..FP
                                             - - - IX- - -
M.CviPI  317  TDRSSHSLPTQVKFSPEGEDGKHLSGKFCAWLMGYDKEYLGNLLEY.
M.CviJI  321  TDRQSHALPTQVRFSYRGVCGRHLSGIWCAWLMGYDQEYLGYLVQYD
M.HaeIII 288  DDFIFHYESLNDGYKMIG.NAVPVN...LAYEIAKTIKSALEICKGN
                       - - - - - X - - - - -
```

Figure 2

Fig. 3A
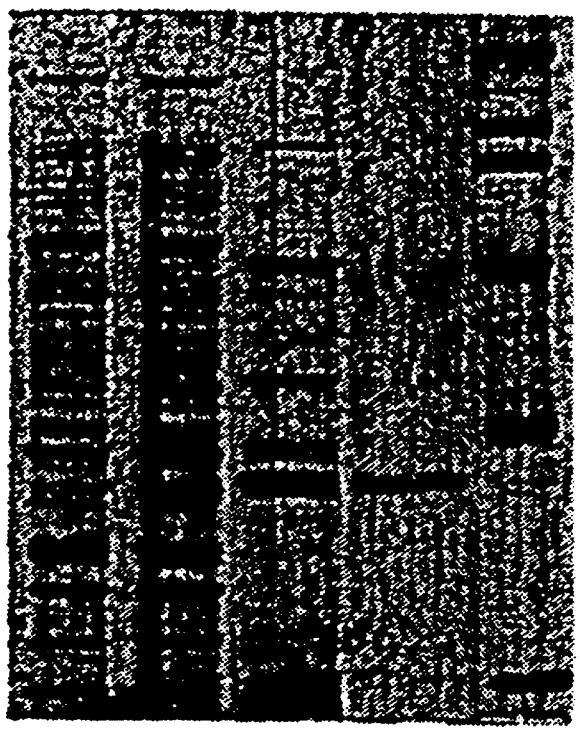
Fig. 3B
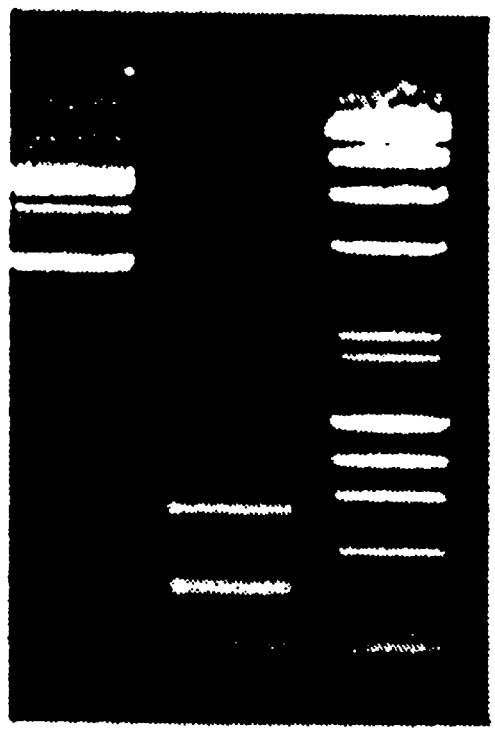
Figure 3

SEQUENCE LISTING

```
<160> NUMBER OF SEQ ID NOS:   12

<210> SEQ ID NO 1
<211> LENGTH: 1141
<212> TYPE: DNA
<213> ORGANISM: Chlorella Virus NYs-1

<400> SEQUENCE: 1
attaattaat agatacgtat atcgaatata tgaccttgaa agcgctcgaa ttattcgccg      60
gaattgcggg aataacgcat ggtcttcgtg gattcgtaga acccgtggct ttcgtcgaga     120
taaacaaaga tgctcaagaa tttctctcta caaagttccc ggataaaccg gtgttcgatg     180
atgtgacgaa attttcaaaa cgtgattttg acgagccgat cgatatgatt accggaggat     240
```

-continued

```
tcccttgcac cggttttagc atagcaggta aacgaaatgg tttcgaacac gcagaatccg    300
gcttattcgg agaagtcgtg cgcataacga aagaatacat gccaaagatg gtcttttag    360 aaaactctgg catgttgagt cacaagtata acttggacat cgtcatcaga tctatggatt    420
ctctaggcta tgattgtcga tgggttactt tgcgagccac agtcgtggga gctttacaca    480
cgagacatcg ttggttctgt ttgtgcacac gtaaagatca tattcgcgaa acgctcattt    540
gcgatcgaga agtcactaag ttcgactggg aaaatgatag acctcctata caggtagact    600
cacgaagcta tgaaaatagt cgtctcgtga gatttgccgg ttattccgtc gttcccgatc    660
aaattcgata tgcattcaca ggtctctaca ccggaaattt ctcaccatcg ttctcgaaga    720
cgctcgtacc aggatcatta gaggaagta tttgtttcaa tgaagacaaa ataacgaacg    780
gatattacaa agatggtgta tattatgaat tcgttcgcac ggagacacac agagaacccg    840
tgaacatact tctgactccg agagaaatac cgaataaaca taacgggaaa aaactgctca    900
ctttaccagt gacgaaaaga tattggtgta ctccttgtgc ttcatacgga aaaggaaccg    960
caggaggcag agtattaaca gaccgttcga gtcattctct tccaactcaa gtgaaatttt    1020
ctcccgaagg agaggacgga aaacatctat ctggaaagtt ttgtgcatgg ctcatgggat    1080
atgacaaaga atatttagga aatttgttag aatattgaat cacaatttgt tctttagacc    1140
c                                                                    1141
```

<210> SEQ ID NO 2
<211> LENGTH: 362
<212> TYPE: PRT
<213> ORGANISM: Chlorella Virus NYs-1

<400> SEQUENCE: 2

```
Met Thr Leu Lys Ala Leu Glu Leu Phe Ala Gly Ile Ala Gly Ile Thr
  1               5                  10                  15

His Gly Leu Arg Gly Phe Val Glu Pro Val Ala Phe Val Glu Ile Asn
             20                  25                  30

Lys Asp Ala Gln Glu Phe Leu Ser Thr Lys Phe Pro Asp Lys Pro Val
         35                  40                  45

Phe Asp Asp Val Thr Lys Phe Ser Lys Arg Asp Phe Asp Glu Pro Ile
 50                  55                  60

Asp Met Ile Thr Gly Gly Phe Pro Cys Thr Gly Phe Ser Ile Ala Gly
 65                  70                  75                  80

Lys Arg Asn Gly Phe Glu His Ala Glu Ser Gly Leu Phe Gly Glu Val
             85                  90                  95

Val Arg Ile Thr Lys Glu Tyr Met Pro Lys Met Val Phe Leu Glu Asn
            100                 105                 110

Ser Gly Met Leu Ser His Lys Tyr Asn Leu Asp Ile Val Ile Arg Ser
        115                 120                 125

Met Asp Ser Leu Gly Tyr Asp Cys Arg Trp Val Thr Leu Arg Ala Thr
    130                 135                 140

Val Val Gly Ala Leu His Thr Arg His Arg Trp Phe Cys Leu Cys Thr
145                 150                 155                 160

Arg Lys Asp His Ile Arg Glu Thr Leu Ile Cys Asp Arg Glu Val Thr
                165                 170                 175

Lys Phe Asp Trp Glu Asn Asp Arg Pro Pro Ile Gln Val Asp Ser Arg
            180                 185                 190

Ser Tyr Glu Asn Ser Arg Leu Val Arg Phe Ala Gly Tyr Ser Val Val
        195                 200                 205
```

```
Pro Asp Gln Ile Arg Tyr Ala Phe Thr Gly Leu Tyr Thr Gly Asn Phe
    210                 215                 220

Ser Pro Ser Phe Ser Lys Thr Leu Val Pro Gly Ser Leu Glu Gly Ser
225                 230                 235                 240

Ile Cys Phe Asn Glu Asp Lys Ile Thr Asn Gly Tyr Tyr Lys Asp Gly
                245                 250                 255

Val Tyr Tyr Glu Phe Val Arg Thr Glu Thr His Arg Glu Pro Val Asn
            260                 265                 270

Ile Leu Leu Thr Pro Arg Glu Ile Pro Asn Lys His Asn Gly Lys Lys
        275                 280                 285

Leu Leu Thr Leu Pro Val Thr Lys Arg Tyr Trp Cys Thr Pro Cys Ala
    290                 295                 300

Ser Tyr Gly Lys Gly Thr Ala Gly Gly Arg Val Leu Thr Asp Arg Ser
305                 310                 315                 320

Ser His Ser Leu Pro Thr Gln Val Lys Phe Ser Pro Glu Gly Glu Asp
                325                 330                 335

Gly Lys His Leu Ser Gly Lys Phe Cys Ala Trp Leu Met Gly Tyr Asp
            340                 345                 350

Lys Glu Tyr Leu Gly Asn Leu Leu Glu Tyr
        355                 360

<210> SEQ ID NO 3
<211> LENGTH: 367
<212> TYPE: PRT
<213> ORGANISM: Chlorella Virus IL-3A

<400> SEQUENCE: 3

Met Ser Phe Arg Thr Leu Glu Leu Phe Ala Gly Ile Ala Gly Ile Ser
1               5                   10                  15

His Gly Leu Arg Gly Ile Ser Thr Pro Val Ala Phe Val Glu Ile Asn
            20                  25                  30

Glu Asp Ala Gln Lys Phe Leu Lys Thr Lys Phe Ser Asp Ala Ser Val
        35                  40                  45

Phe Asn Asp Val Thr Lys Phe Thr Lys Ser Asp Phe Pro Glu Asp Ile
    50                  55                  60

Asp Met Ile Thr Ala Gly Phe Pro Cys Thr Gly Phe Ser Ile Ala Gly
65                  70                  75                  80

Ser Arg Thr Gly Phe Glu His Lys Glu Ser Gly Leu Phe Ala Asp Val
                85                  90                  95

Val Arg Ile Thr Glu Glu Tyr Lys Pro Lys Ile Val Phe Leu Glu Asn
            100                 105                 110

Ser His Met Leu Ser His Thr Tyr Asn Leu Asp Val Val Lys Lys
        115                 120                 125

Met Asp Glu Ile Gly Tyr Phe Cys Lys Trp Val Thr Cys Arg Ala Ser
130                 135                 140

Ile Ile Gly Ala His His Gln Arg His Arg Trp Phe Cys Leu Ala Ile
145                 150                 155                 160

Arg Lys Asp Tyr Glu Pro Glu Glu Ile Ile Val Ser Val Asn Ala Thr
                165                 170                 175

Lys Phe Asp Trp Glu Asn Asn Glu Pro Pro Cys Gln Val Asp Asn Lys
            180                 185                 190

Ser Tyr Glu Asn Ser Thr Leu Val Arg Leu Ala Gly Tyr Ser Val Val
        195                 200                 205

Pro Asp Gln Ile Arg Tyr Ala Phe Thr Gly Leu Phe Thr Gly Asp Phe
    210                 215                 220
```

Glu Ser Ser Trp Lys Thr Thr Leu Thr Pro Gly Thr Ile Ile Gly Thr
225                 230                 235                 240

Glu His Lys Lys Met Lys Gly Thr Tyr Asp Lys Val Ile Asn Gly Tyr
                245                 250                 255

Tyr Glu Asn Asp Val Tyr Tyr Ser Phe Ser Arg Lys Glu Val His Arg
            260                 265                 270

Ala Pro Leu Asn Ile Ser Val Lys Pro Arg Asp Ile Pro Glu Lys His
        275                 280                 285

Asn Gly Lys Thr Leu Val Asp Arg Glu Met Ile Lys Lys Tyr Trp Cys
290                 295                 300

Thr Pro Cys Ala Ser Tyr Gly Thr Ala Thr Ala Gly Cys Asn Val Leu
305                 310                 315                 320

Thr Asp Arg Gln Ser His Ala Leu Pro Thr Gln Val Arg Phe Ser Tyr
                325                 330                 335

Arg Gly Val Cys Gly Arg His Leu Ser Gly Ile Trp Cys Ala Trp Leu
            340                 345                 350

Met Gly Tyr Asp Gln Glu Tyr Leu Gly Tyr Leu Val Gln Tyr Asp
        355                 360                 365

<210> SEQ ID NO 4
<211> LENGTH: 330
<212> TYPE: PRT
<213> ORGANISM: Haemophilus influenzae

<400> SEQUENCE: 4

Met Asn Leu Ile Ser Leu Phe Ser Gly Ala Gly Gly Leu Asp Leu Gly
1               5                   10                  15

Phe Gln Lys Ala Gly Phe Arg Ile Ile Cys Ala Asn Glu Tyr Asp Lys
                20                  25                  30

Ser Ile Trp Lys Thr Tyr Glu Ser Asn His Ser Ala Lys Leu Ile Lys
            35                  40                  45

Gly Asp Ile Ser Lys Ile Ser Ser Asp Glu Phe Pro Lys Cys Asp Gly
50                  55                  60

Ile Ile Gly Gly Pro Pro Cys Gln Ser Trp Ser Glu Gly Gly Ser Leu
65                  70                  75                  80

Arg Gly Ile Asp Asp Pro Arg Gly Lys Leu Phe Tyr Glu Tyr Ile Arg
                85                  90                  95

Ile Leu Lys Gln Lys Lys Pro Ile Phe Phe Leu Ala Glu Asn Val Lys
            100                 105                 110

Gly Met Met Ala Gln Arg His Asn Lys Ala Val Gln Glu Phe Ile Gln
        115                 120                 125

Glu Phe Asp Asn Ala Gly Tyr Asp Val His Ile Ile Leu Leu Asn Ala
130                 135                 140

Asn Asp Tyr Gly Val Ala Gln Asp Arg Lys Arg Val Phe Tyr Ile Gly
145                 150                 155                 160

Phe Arg Lys Glu Leu Asn Ile Asn Tyr Leu Pro Pro Ile Pro His Leu
                165                 170                 175

Ile Lys Pro Thr Phe Lys Asp Val Ile Trp Asp Leu Lys Asp Asn Pro
            180                 185                 190

Ile Pro Ala Leu Asp Lys Asn Lys Thr Asn Gly Asn Lys Cys Ile Tyr
        195                 200                 205

Pro Asn His Glu Tyr Phe Ile Gly Ser Tyr Ser Thr Ile Phe Met Ser
210                 215                 220

Arg Asn Arg Val Arg Gln Trp Asn Glu Pro Ala Phe Thr Val Gln Ala

```
                225                 230                 235                 240
Ser Gly Arg Gln Cys Gln Leu His Pro Gln Ala Pro Val Met Leu Lys
                245                 250                 255

Val Ser Lys Asn Leu Asn Lys Phe Val Glu Gly Lys Glu His Leu Tyr
            260                 265                 270

Arg Arg Leu Thr Val Arg Glu Cys Ala Arg Val Gln Gly Phe Pro Asp
        275                 280                 285

Asp Phe Ile Phe His Tyr Glu Ser Leu Asn Asp Gly Tyr Lys Met Ile
    290                 295                 300

Gly Asn Ala Val Pro Val Asn Leu Ala Tyr Glu Ile Ala Lys Thr Ile
305                 310                 315                 320

Lys Ser Ala Leu Glu Ile Cys Lys Gly Asn
                325                 330

<210> SEQ ID NO 5
<211> LENGTH: 21
<212> TYPE: DNA
<213> ORGANISM: Artificial Sequence
<220> FEATURE:
<223> OTHER INFORMATION: Synthetic Sequence
<223> OTHER INFORMATION: at position 10, n represents any nucleotide
<223> OTHER INFORMATION: at position 16, n represents any nucleotide
<223> OTHER INFORMATION: at position 19, n represents any nucleotide

<400> SEQUENCE: 5
ccggatcctn ttygcnggna t                                                 21

<210> SEQ ID NO 6
<211> LENGTH: 29
<212> TYPE: DNA
<213> ORGANISM: Artificial Sequence
<220> FEATURE:
<223> OTHER INFORMATION: Synthetic Sequence
<223> OTHER INFORMATION: at position 12, n represents any nucleotide
<223> OTHER INFORMATION: at position 21, n represents any nucleotide
<223> OTHER INFORMATION: at position 27, n represents any nucleotide

<400> SEQUENCE: 6
acctgcagra anccytgrca nggraancc                                         29

<210> SEQ ID NO 7
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 7
ccattcaacc caaccactac ac                                                22

<210> SEQ ID NO 8
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 8
gggttttgtg gtattattgt agtattgg                                          28

<210> SEQ ID NO 9
<211> LENGTH: 31
<212> TYPE: DNA
<213> ORGANISM: Artificial Sequence
```

-continued

```
<220> FEATURE:
<223> OTHER INFORMATION: Synthetic Sequence

<400> SEQUENCE: 9
tacctaactc cccatcatat aaataactac a                              31

<210> SEQ ID NO 10
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 10
tttttagaat gatttggttg agtatttatt ag                             32

<210> SEQ ID NO 11
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 11
ctaattataa ttcacaaata cacctcaaaa a                              31

<210> SEQ ID NO 12
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 12
aagttaggtt atttttgatg gttttattg                                 29
```

US 6,492,168 B1

METHYLTRANSFERASE GENE AND ENZYME

This application claims priority to U.S. Provisional Application Serial No. 60/082,674, filed Apr. 22, 1998, which is incorporated by reference herein.

Pursuant to 35 U.S.C. §202(c), it is acknowledged that the U.S. Government has certain rights in the invention described herein, which was made in part with funds from the National Institutes of Health, Grant No. GM52908.

FIELD OF THE INVENTION

The present invention relates to the field of analysis and manipulation of chromosomal DNA in situ. In particular, the invention provides a novel cytosine methyltransferase gene and encoded enzyme that recognizes the dinucleotide GpC, and its use in high resolution analysis and manipulation of protein-DNA interactions in chromatin.

BACKGROUND OF THE INVENTION

Various publications or patents are referenced in this application to describe the state of the art to which the invention pertains. Each of these publications or patents is incorporated by reference herein.

In vivo methylation of DNA has been used successfully to study protein-DNA interactions in the chromatin of living cells. A high frequency of methyltransferase targets is critical for high resolution mapping of chromatin structure. Among currently available methyltransferase probes, the only de novo dinucleotide methyltransferase is M.SssI, which recognizes a CpG site (Renbaum, P., Abrahamove, D., Fainsod, A., Wilson, G., Rottem, S. and Razin, A. (1990) *Nucleic Acids Res.*, 18, 1145–1152). Due to underrepresentation of the CpG dinucleotide in the genome, the resolution of chromatin structure maps using this enzyme is about 35 base pairs on average in *S. cerevisiae* (Dujon, B., Alexandrakl, D., André, B., Ansorge, W., Baladron, V., Ballesta, J. P. G., Banrevl, A., Bolle, P. A., Bolotin-Fukuhara, M., Bossler, P. et al). (1994) *Nature*, 369, 371–378.). With this moderate level of resolution, M.SssI can possibly serve to detect the presence of a positioned nucleosome, 146 bp in yeast, without the need for introduction of additional CpG sites into native DNA sequences. However, this resolution is insufficient for mapping the interactions of non-histone regulatory proteins, since the typical length of the target DNA sequence of most regulatory proteins is ~20–30 base pairs or less. For example, the yeast TATA box binding protein (TBP) recognizes and binds to an 8 bp sequence (Kim, Y., Geiger, J. H., Hahn, S. and Sigler, P. B. (1993) *Nature*, 365, 512–520.), while the well-characterized transcriptional activator Gal4p binds to a 17 bp consensus sequence (Giniger, E., Varnum, S. M. and Ptashne, M. (1985) *Cell*, 40, 767–774.). Furthermore, methylation of CpG islands has been implicated as an important controlling element for gene regulation in mammalian systems, which may limit the application of M.SssI in higher organisms (Tazi, J. and Bird, A. (1990) *Cell*, 60, 909–920.). To address both the limitation of resolution and the possible inability to utilize M.SssI in higher organisms, cloning and expression of cytosine-5-DNA methyltransferases (5-$^{me}$C MTase) with different specificities but similarly small recognition sites is essential.

A family of double-stranded DNA viruses that infect certain unicellular, eukaryotic, Chlorella-like green algae are reported to be a rich source of restriction/ modification systems (Nelson, M., Zhang, Y. and Van Etten, J. L. (1993) *DNA Methylation: Molecular Biology and Biological Significance*. Birkhauser-Verlag Press, Basel, Switzerland, pp. 186–211; Nelson, M., Burbank, D. E. and Van Etten, J. L. (1998) *Biological Chem.* 379, 423–428). Among the 37 viruses infecting Chlorella NC64A and the five viruses infecting Chlorella Pbi which have been partially characterized, 39 viral DNAs contain 5-methylcytosine, ranging in concentration from 0.1 to 47% of total cytosine (Nelson & Van Etten, 1993, supra; Nelson & Van Etten, 1998, supra)

One cytosine methyltransferase, M.CviJI, has been cloned from Chlorella virus IL-3A and shown to recognize the nucleotide sequence RGC(T/C/G) (Shields, S. L., Burbank, D. E., Grabherr, R. and Van Etten, J. L. (1990) *Virology*, 176, 16–24). As determined by the resistance/sensitivity of the viral DNAs to over 70 methylation-sensitive restriction endonucleases, at least five independent 5-$^{me}$C modification systems are predicted to be encoded by some of the more highly modified viruses, including methyltransferases thought to recognize Cpc and RpCpY (Nelson & Van Etten, 1993, supra;Nelson & Van Etten, 1998, supra) . Based on the composition of the yeast genome as an example, on average, one Cpc site per 13.9 bp and one RpCpY site per 10.7 bp can be expected in the genome. Achieving this level of resolution would allow mapping the interactions of most non-histone, regulatory proteins. The cloning of methyltransferases from Chlorella viruses could greatly extend the resolution of chromatin mapping as well as allow extension of in vivo chromatin mapping to higher organisms.

SUMMARY OF THE INVENTION

The present invention provides a novel cytosine-5-DNA methyltransferase gene and its encoded enzyme, isolated from Chlorella virus NYs-1, that recognizes the sequence GpC. This methyltransferase having a small recognition site that occurs with a high frequency in eukaryotic genomes is of particular utility for high resolution analysis of chromatin structure and protein-DNA interactions in living cells.

According to one aspect of the invention, an isolated nucleic acid molecule is provided, which encodes a cytosine-5 DNA methyltransferase that recognizes a GpC dinucleotide in DNA. Preferably, the nucleic acid molecule is isolated from a Chlorella virus, most preferably from Chlorella virus NYs-1. In a preferred embodiment, the encoded cytosine-5 DNA methyltransferase has an amino acid sequence substantially the same as SEQ ID NO:2 and the encoded methyltransferase is catalytically active and recognizes the GpC dinucleotide. Most preferably, the encoded cytosine-5 DNA methyltransferase has amino acid SEQ ID NO:2.

The following isolated nucleic acid sequences are provided in the present invention: (a) SEQ ID NO:1; (b) natural variants of SEQ ID NO:1; (c) sequences that hybridize with part or all of an antisense strand of SEQ ID NO:1 and encode part or all of a protein having a catalytic activity and sequence recognition specificity the same as the protein having SEQ ID NO:2; and (d) a sequence encoding part or all of SEQ ID NO:2.

According to another aspect of the invention, a recombinant DNA molecule comprising one of the aforementioned cytosine methyltransferase-encoding nucleic acid molecules inserted into a vector for transforming cells, is provided. The recombinant DNA molecule is used to transform cells, which may be cultured cells or which may be cells of a living organism. Oligonucleotides of between about 10 to about 100 nucleotides in length which hybridize with portions of the methyltransferase-encoding nucleic acid molecule are also provided in accordance with the present invention, as are antibodies immunologically specific for part or all of the encoded polypeptide.

According to another aspect of the invention, an isolated cytosine-5 DNA methyltransferase that specifically recognizes a GpC dinucleotide sequence in DNA is provided. The methyltransferase preferably is isolated from a Chlorella virus, most preferably virus NYs-1. In a preferred embodiment, the cytosine-5 DNA methyltransferase has an amino acid sequence substantially the same as SEQ ID NO:2 and the methyltransferase is catalytically active and recognizes the GpC dinucleotide. In a particularly preferred embodiment, the enzyme has amino acid SEQ ID NO:2.

According to another aspect of the invention methods of mapping DNA-protein interactions with the novel cytosine methyltransferase are provided. One method comprises the steps of: (a) providing a sample of the cells transformed with a nucleic acid molecule that encodes the novel cytosine-5 methyltransferase; (b) growing a test culture of the transformed cells under conditions enabling production of the methyltransferase; (c) growing a control culture of equivalent cells that do not produce the methyltransferase; (d) isolating the DNA from the test culture and the control culture; (e) exposing the DNA from the control culture to the cytosine-5 methyltransferase; and (f) comparing the cytosine methylation of the DNA from the test culture with the cytosine methylation of the DNA from the control culture, a decrease in extent of methylation in the DNA of the test culture being proportional to the amount of DNA-protein interaction occurring in the DNA in the cell. The method may further include comparing a pattern of methylation in a selected region of the DNA from the test culture and the control culture, a change in the methylation pattern in the respective DNA being indicative of a location of a DNA-protein interaction in the DNA of the cell. In one embodiment, the aforementioned method is applied to analyzing interactions between nucleosome proteins and chromosomal DNA. In another embodiment, the method is applied to analyzing an interaction between a transcriptional regulatory protein and a transcriptional response element in the DNA. These methods are used to advantage in the high resolution mapping of sites of interest for in situ genetic manipulation, such as insertion of a foreign gene for gene therapy.

These and other features and advantages of the present invention will be described in greater detail in the description and examples set forth below.

BRIEF DESCRIPTION OF THE DRAWINGS

FIGS. 1A and 1B. M.CviPI methylates GpC sites in *E.coli*. Plasmid pETNYs-1-5, containing the coding sequence of M.CviPI, or pET20b+, the parent vector, was purified from IPTG-induced *E.coli* cells. 5-$^{me}$C residues on the lower strand were identified in isolated DNA by deamination, subsequent PCR amplification and direct cycle sequencing of the purified PCR products. FIG. 1A and FIG. 1B show two different sequence regions that were investigated, which include GpC sites with all 16 possible combinations of flanking bases. In FIG. 1A, lanes 1–4 are the sequencing lanes of the region investigated using the PCR product used in lane 5 as template. Lane 5 is a negative control where the same sequence region was examined in the pET20b+ vector only sample. The last lane is the methylation pattern of PETNYs-1-5 isolated from induced cells expressing M.CviPI. In (b), the first four lanes (lanes 1–4) are sequencing lanes while the last two lanes (lanes 5 and 6) represent the methylation pattern of pETNYs-1-5 isolated from two different induction experiments. In both parts, the arrow represents artefactual primer extension pauses which occurred in samples from both pET20b+ and pETNYs-1-5. The asterisks indicate every GpC site in the sequence that is resolvable on the gel. The flanking bases are listed 5'→3' beside each methylation band. Due to the fact that methylation of the lower strand was analyzed, the sequence context can be ascertained by reading the gel from the top to the bottom.

FIG. 2. Protein sequence alignment of three cytosine MTases, M.CviPI (SEQ ID NO:2), M.CviJI (SEQ ID NO:3) and M.HaeIII (SEQ ID NO:4), by CLUSTLW (Thompson, J. D. et al., *Nuc. Acids Res.* 22, 4673–4680, 1994). The bars above the sequence represent the regions of conserved motifs, as indicated. The putative target recognition domain is a indicated by a dashed bar above the sequence Motifs IX and X of M.HaeIII are indicated by dashed bars below the sequence; these domains appear not to be conserved in the two Chlorella virus MTases. Residues that are identical in all three proteins are indicated in bold. All other residues, including similar residues, are in plain text. The regions utilized to create the two degenerate PCR primers are indicated by arrows (only the portion of the primer that is complementary to the MTase gene is indicated).

FIGS. 3A and 3B. Purification of M.CviPI and assay for activity in vitro. FIG. 3A: SDS-polyacrylamide gel showing the proteins after each step of purification. From 1 1 of non-induced (lane 1) or IPTG-induced (lane 2) cells, total protein from 40 and 20 µl cells, respectively, was extracted and analyzed on the gel. Lane 3 contains 10 µl of the 200 µl total eluate from the Ni$^{2+}$-agarose column. The final, purified enzyme eluted with 0.3–0.4 M NaCl from the phosphocellulose column was analyzed in lane 4 (10 µl of 200 µl total eluate). The arrow indicates the position of the enzyme band. The molecular weight marker used was the broad range standard from Bio-Rad; the 200, 116, 97.4, 66, 45 and 31 kDa species are visible. FIG. 3B: In vitro MTase assay of purified M.CviPI after phosphocellulose column chromatography. Purified enzyme [1 µl of the 200 µl phosphocellulose eluate analyzed in lane 4 of (a)] was assayed for MTase activity as described in Materials and Methods. pTZ18U DNA (1 µg) was treated with the enzyme in the presence of Ado-Met and subsequently digested with HaeIII (lane 1). As a control, the same reaction was performed in the absence of Ado-Met (lane 2). The molecular marker is a [lambda]/HindIII plus [phis]X174RF/HaeIII digestion mixture. Note the resistance to digestion by the methylation-sensitive restriction endonuclease in the sample treated with M.CviPI and Ado-Met.

DETAILED DESCRIPTION OF THE INVENTION

I. Definitions

Figure 4:
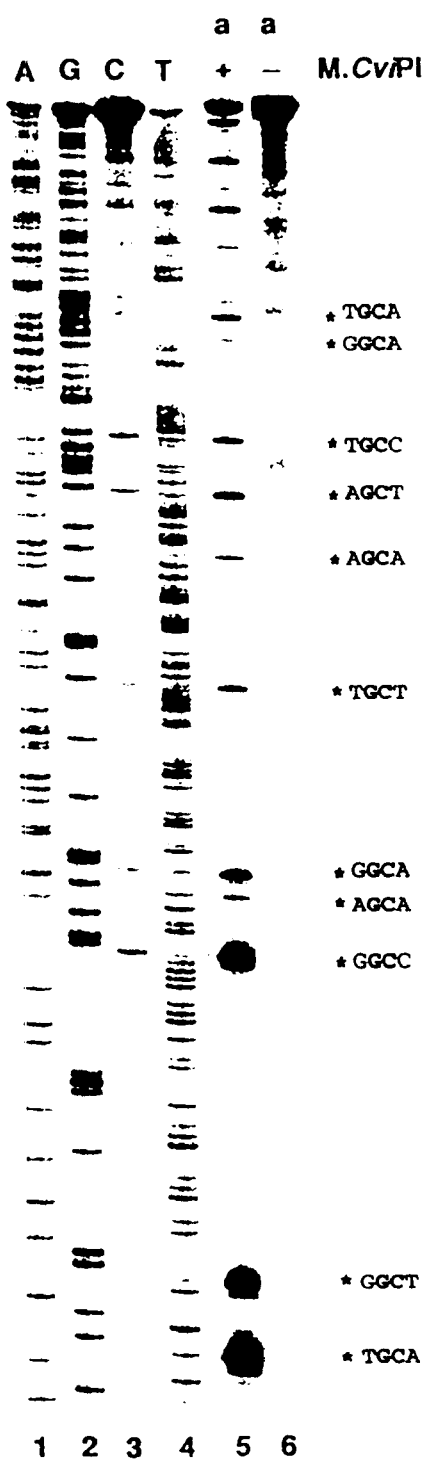
FIG. 4. Methylation activity of M.CviPI expressed in yeast. Genomic DNA was purified from yeast cells grown in medium containing galactose and subsequently deaminated to determine the methylation pattern. Lanes 1–4 contain the sequencing lanes for 45871–45331 m.u. of chromosome XI, a region near the 3'-end of the coding sequence of STE6. The methylation pattern of DNAs purified from MXY108 yeast cells is shown in lane 5. Every GpC site present in the region (indicated by the asterisks followed by the GpC site and its flanking bases) is modified by the methyltransferase. As a control, DNA isolated from the parental a cell line, lacking the methyltransferase gene, is devoid of methylation (lane 6), demonstrating that the MTase activity is encoded by the M.CviPI gene.

Various terms relating to the biological molecules of the present invention are used hereinabove and also throughout the specification and claims.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to proteins or peptides, the term "isolated protein (or peptide)" or "isolated and purified protein (or peptide)" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. In the comparisons made in the present invention, the CLUSTLW program and parameters employed therein were utilized (Thompson et al., 1994, supra). However, equivalent alignments and similarity/identity assessments can be obtained through the use of any standard alignment software. For instance, the GCG Wisconsin Package version 9.1, available from the Genetics Computer Group in Madison, Wisconsin, and the default parameters used (gap creation penalty=12, gap extension penalty=4) by that program may also be used to compare sequence identity and similarity.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell. In particular, as used herein, the term "DNA transcriptional response element" refers to a DNA sequence specifically recognized for binding by a DNA binding protein characterized as a transcriptional regulator (either activator or suppressor).

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

II. Description

The present invention provides a novel cytosine-5-DNA methyltransferase that recognizes the dinucleotide GpC. A gene encoding the novel methyltransferase was cloned from Chlorella virus NYs-1. It was found to be expressed, active and specific for the GpC dinucleotide in any context in both *Escherichia coli* and *Saccharomyces cerevisiae*, as described in detail in Example 3.

The novel methyltransferase, referred to herein as M.CviPI, is believed to be the first and only cytosine methyltransferase identified and isolated, which recognizes the GpC dinucleotide. The only other currently available de novo dinucleotide methyltransferase is M.SssI, which recognizes a CpG site (Renbaum et al., 1990, supra). However, due to under-representation of the CpG dinucleotide in the genome, the ~35 bp resolution of chromatin structure maps using this enzyme is insufficient for mapping the interactions of non-histone regulatory proteins, most of which have target DNA sequences of ~20–30 base pairs or less. Moreover, the M.SssI enzyme may not be appropriate for use mammalian chromatin analysis, due to the fact that methylation of CpG islands has been implicated as an important controlling element for gene regulation in mammalian systems (Tazi et al., 1990 supra).

The gene encoding M.CviPI was isolated from a genomic library of the NYs-1 Chlorella virus using synthetic PCR primers designed from highly conserved cytosine methyltransferase sequence motifs, as described in greater detail in Examples 1 and 2. The gene was sequenced and a predicted polypeptide of 362 amino acids with a molecular weight of 41,903 Da was identified. The nucleotide sequence of the gene encoding M.CviPI is set forth herein as SEQ ID NO:1. The deduced amino acid sequence of M.CviPI is set forth herein as SEQ ID NO:2. Both sequences are available in public databases, e.g., DDBJ, EMBL, and GenBank as Accession No. AF062394.

The M.CviPI protein contains several amino acid motifs with high similarity to those of other known 5-methylcytosine-forming methyltransferases (Kumar, S. et al. (1993) *Nucl. Acids Res.* 22: 1–10). An alignment of the amino acid sequence of M.CviPI with two methyltransferase of similar sequence (M.CviJI from a Chlorella virus, recognizing RGC(T/C/G) and M.HaeIII, a bacterial enzyme recognizing GGCC) is shown in FIG. 2. As can be seen, conserved sequence motifs found generally in cytosine methyltransferases can also be found, to a greater or lesser extent, in M.CviPI, with the exception of motifs IX and X. These motifs in the carboxyl portion of the protein are apparently not conserved in M.CviPI or in the other Chlorella virus methyltransferase, M.CviJI.

The variable region between motifs VIII and IX is known to define the sequence specificity of both mono-specific and multi-specific m5-C methyltransferases (see Kumar et al, 1993, supra and references cited therein) and, for this reason, is sometimes referred to as the "target recognition domain" (TRD). Additionally, motif IX has extensive interaction with the variable region and is likely to be involved in sequence-specific recognition. While not intending to be limited by any explanation of mechanism of action, the unique sequence specificity of M.CviPI, the only methyltransferase found to recognize GpC in any context, may be reflected in the lack of sequence conservation in the variable region and in motif IX. Thus, the deduced amino acid sequence of M.CviPI indicates that it forms a protein of the same general structure as other m5-C methyltransferases, especially as relates to the catalytic site. However, M.CviPI (as well as the other Chlorella virus methyltransferase, M.CviJI) does not possess much sequence conservation in the C-terminal region comprising the TRD, motif IX and motif X, and therefore likely varies from other methyltransferases in the region defining DNA sequence specificity.

We anticipate a number of applications for the novel M.CviPI gene its encoded protein, many of which are based on its utility for high-resolution chromatin mapping. Such applications are described in greater detail below.

Although the M.CviPI gene from Chlorella virus NYs-1 is described and exemplified herein, this invention is intended to encompass nucleic acid sequences and proteins from other organisms, including plants, yeast, insects and mammals, that are sufficiently similar to be used instead of the Chlorella virus NYs-1 nucleic acid and proteins for the purposes described below. These preferably include, but are not limited to, natural variants or mutants of SEQ ID NO:1, which are likely to be found in (1) different isolates of Chlorella virus NYs-1 and (2) equivalent GpC dinucleotide cytosine methyltransferases isolated from other Chlorella viruses, including sub-groups of NC64A viruses (of which NYs-1 is a member) and sub-groups of Pbi viruses (see Nelson et al., 1993, supra for a list of Chlorella viruses). Because such variants are expected to possess certain differences in nucleotide and amino acid sequence, this invention provides an isolated M.CviPI nucleic acid molecule having at least about 70% (preferably 80% and more preferably over 90%) sequence homology across SEQ ID NO:1 (and, most preferably, specifically comprising the coding region of SEQ ID NO:1). This invention also provides isolated polypeptide products of the open reading frames of SEQ ID NO:1, having at least about 70% (preferably 80% or 90% or greater) sequence homology with the amino acid sequences of SEQ ID NO:2. Because of the natural sequence variation likely to exist among M.CviPI genes, one skilled in the art would expect to find up to about 20–30% nucleotide sequence variation, while still maintaining the unique properties of the M.CviPI encoded polypeptide of the present invention. Such an expectation is due in part to the degeneracy of the genetic code, as well as to the known evolutionary success of conservative amino acid sequence variations, which do not appreciably alter the nature of the encoded protein, particularly the novel sequence specificity of M.CviPI. Accordingly, such variants are considered substantially the same as one another, and are included within the scope of the present invention.

In particular, the present invention includes variants of SEQ ID NO:1 or SEQ ID NO:2 which share similarity with the regions of those sequences encoding or comprising the variable region between motif VIII and IX or motif IX itself. These include the regions of SEQ ID NO:2 corresponding to residues 200 to the carboxyl terminus, and preferably: (1) residues 218–248, the putative TRD; and (2) residues 276–291 (inclusive), corresponding to motif IX. In SEQ ID NO: 1, these include the region from about nucleotide 630 to the stop. codon, and preferably: (1) between about nucleotides 684 to 774 (inclusive) encoding the putative TRD; and (2) between about nucleotides 858 to 903 (inclusive) encoding the region corresponding to motif IX. As discussed above, the uniqueness of these regions of M.CviPI likely reflects the functional uniqueness of the enzyme in recognizing the GpC dinucleotide.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al.") are used.

A. Preparation of M.CviPI Nucleic Acid Molecules, encoded Polypeptides and Immunospecific Antibodies 1. Nucleic Acid Molecules M.CviPI nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide and amino acid sequence information, such as SEQ ID NO:1 and SEQ ID NO:2, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Variants of SEQ ID NO:1 also may be synthesized as described above. For instance, in some cases it may be advantageous to customize a nucleic acid molecule encoding SEQ ID NO:2 or function equivalent thereof for expression in cells of a particular species. In this case, SEQ ID NO: 2 may be back-translated using a computer program that substitutes appropriate codon preferences for the selected species, as well as any other features known to enhance gene expression in that species. Codon preference tables for a wide variety of species are publicly available as are programs for performing such reverse translations. In a particularly preferred embodiment, the back-translated nucleic acid molecule encodes SEQ ID NO:2. In another preferred embodiment, it encodes a variant of SEQ ID NO:2 wherein selected residues of the polypeptide comprise conservative substitutions for the corresponding residue found in SEQ ID NO:2.

M.CviPI genes also may be isolated from appropriate biological sources using methods known in the art. In the exemplary embodiment of the invention, the M.CviPI clone having SEQ ID NO:1 was isolated from a genomic library of Chlorella virus NYs-1. Genomic libraries of other NYs-1 isolates and other Chlorella viruses are also suitable sources for isolating the GpC dinucleotide methyltransferase of the present invention. A preferred means for isolating M.CviPI genes is PCR amplification using genomic templates and M.CviPI-specific primers derived from SEQ ID NO:1. In this embodiment, a preferable region from which to construct such primers is the "variable" region between motifs VIII and IX, as well as motif IX itself which respectively comprise sequence encoding residues 218–248 and 276–291 of SEQ ID NO:2. Inasmuch as the GpC specificity of the methyltransferase of the invention is a significant novel feature of the enzyme, and this feature is believed to be specified, at least in part, by the variable region of the protein and/or by motif IX, these regions are considered particularly suitable for design of PCR primers to isolate other GpC-recognizing methyltransferases from other biological sources.

In accordance with the present invention, nucleic acids having the appropriate level sequence homology with part or all the coding regions of SEQ ID NO:1 may be identified by using hybridization and washing conditions of appropriate stringency. For example, hybridizations may be performed, according to the method of Sambrook et al., using a hybridization solution comprising:5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45–55° in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$T_m = 81.5° C. + 16.6 \log[Na+] + 0.41(\% G+C) - 0.63(\% \text{formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the sequences of the present invention.

Nucleic acids of the present invention may be maintained as DNA in any convenient cloning vector. In a preferred embodiment, clones are maintained in plasmid cloning/expression vector, such as pTZ18U for cloning and sequencing) or pET20b+ (Novagen) (for expression of histagged proteins), either of which is propagated in a suitable E. coli host cell. It is preferable that the E. coli host selected to propagate these vectors is one in which a high level of cytosine methylation is not toxic. One suitable strain is E. coli DH5αmut10, which lacks the mcrABC and mrr genes.

In a preferred embodiment, the M.CviPI gene has been cloned into the pYES2 expression vector (Invitrogen) This vector allows a higher level expression of a cDNA insert from the strong, galactose-inducible S. cerevisiae promoter, GAL1. The plasmid also exists as an episome due to inclusion of a 2 micron origin of DNA replication, which allows the plasmid to be maintained at approximately 20 copies per cell. Expression of the enzyme from this vector is roughly estimated to be increased by about 10-fold, as compared with constitutively expressed protein.

M.CviPI nucleic acid molecules of the invention include DNA, RNA, and fragments thereof which may be single- or double-stranded. Thus, this invention provides oligonucleotides (sense or antisense strands of DNA or RNA) of between about 10 to about 100 nucleotides in length, having sequences capable of hybridizing with at least one sequence of a nucleic acid molecule of the present invention, such as selected segments of the DNA having SEQ ID NO: 1. Such oligonucleotides are useful as probes for detecting M.CviPI genes or MRR in test samples, e.g. by PCR amplification, or for the positive or negative regulation of expression of M.CviPI genes at or before translation of the mRNA into proteins.

The M.CviPI promoter and other expression regulatory sequences for M.CviPI are also expected to be useful in connection with the present invention for a variety of purposes apparent to persons skilled in the art. Accordingly, these sequences are also considered within the scope of the present invention.

2. Proteins

Polypeptides encoded by M.CviPI nucleic acids of the invention may be prepared in a variety of ways, according to known methods. If produced in situ the polypeptides may be purified from appropriate sources, e.g., virus preparations.

Alternatively, the availability of nucleic acid molecules encoding the polypeptides enables production of the proteins using in vitro expression methods known in the art. For example, a gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of M.CviPI-encoded polypeptide may be produced by expression in a suitable procaryotic or eucaryotic system. For example, part or all of a DNA molecule, such as the coding portion of SEQ ID NO:1, may be inserted into a plasmid vector adapted for expression in a bacterial cell (such as E. coli as described above) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

A *Saccharomyces cerevisiae* expression system is employed in a preferred embodiment of the invention because of the utility of this organism for chromatin mapping by methyltransferases, due to its lack of natural cytosine methylation. Vectors and strains of S. cerevisiae useful for this purpose are well known in the art, and preferred systems are described in greater detail below.

The M.CviPI polypeptide produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners. In a preferred embodiment, an expression system is used in which a histagged protein is produced, then separated from cellular contents and media. This method is also commonly used.

The M.CviPI-encoded polypeptides of the invention, prepared by the aforementioned methods, may be analyzed according to standard procedures to determine physical characteristics of the expressed protein (e.g., molecular weight, isoelectric point, amino acid composition, amino acid sequence). Methods for analyzing the functional activity also are available. For instance, the location and extent of cytosine methylations in a DNA strand are identified by the bisulfite sequencing method of Frommer et al. (Frommer, M., Macdonald, L. E., illar, D. S., Collis, C. M., Watt, F., Grigg, G. W., Molloy, P. L. and Paul, C. L. (1992) *Proc. Natl Acad. Sci.* USA, 89, 1827–1831), as described in detail in Example 1.

Polypeptides of the present invention include the isolated cytosine-5 DNA methyltransferase described above, as well as fragments of the polypeptide. Such fragments are useful for a variety of purposes known in the art, one of which is the production of specific antibodies, as described below. Nucleic acid sequences encoding such protein fragments are also included in the present invention.

The present invention also provides antibodies capable of immunospecifically binding to polypeptides of the invention. Polyclonal or monoclonal antibodies directed toward the polypeptide encoded by M.CviPI may be prepared according to standard methods. Monoclonal antibodies may be prepared according to general methods of Köhler and Milstein, following standard protocols. In a preferred embodiment, antibodies are prepared, which react immunospecifically with various epitopes of the M.CviPI-encoded polypeptides, such as those comprising the active site(s) or specificity-conferring region(s) of the enzyme.

The present invention also provides transformed cells that comprise part or all of the unique methyltransferase gene of the present invention. These cells can be cultured cells, or they can be cells of a living organism, including but not limited to, bacteria, fungi, unicellular organisms, insects and other invertebrates, vertebrates (including mammals) and plants.

B. Uses of M.CviPI Nucleic Acids, Encoded Proteins and Antibodies

The M.CviPI methyltransferase gene and enzyme of the present invention have primary and fundamental utility for high resolution analysis and manipulation of protein-DNA interactions in living cells. DNA methyltransferases have been developed recently as an alternative method for mapping such protein-DNA interactions because they fulfill several desirable criteria when compared with mapping techniques employing endonucleases: (1) they can be expressed in vivo and, at the low levels of modification employed for mapping, do not impair cell viability; (2) the method eliminates the need for isolation of nuclei with attendant risk of losing labile chromatin constituents; (3) DNA is not damaged by the probe; and (4) detection of both histone-DNA and non-histone regulatory protein-DNA interactions is possible.

Methyltransferases that modify cytosine are preferred for the mapping methods described above because of the availability of a positive chemical display method for detection and quantification of $5^{me}C$ devised by Frommer et al. (1996, supra). Prior to the present invention, the enzyme of choice for modifying cytosine was M.SssI, which suffers from limited resolution due to under-representation of the CpG target in the genome. By contrast, the GpC target sequence recognized by M.CviPI occurs with a frequency of one site every ~15 base pairs in *S. cerevisiae*, the organism exemplified herein to demonstrate the utility of the enzyme for chromatin structure mapping. The effective increase in mapping resolution is at least four-fold, given the clustering of CpG sites. When used in combination with other cytosine methyltransferases, M.CviPI enables a resolution statistically on the order of about one natural site every 10–15 bp.

A preferred embodiment of chromatin mapping utilizes *Saccharomyces cerevisiae*, as described in detail in Examples 1 and 3. The M.CviPI gene, alone or in combination with other methyltransferase-encoding genes, is operably linked to an inducible promoter (e.g., responding to galactose in the growth medium) and integrated into an appropriate locus (e.g., LYS2) in the *S. cerivisiae* genome. Cells are grown to mid- to late log phase in medium containing the inducer, to enable expression of the methyltransferase(s). DNA is rapidly isolated (see Simpson, R T (1998) METHODS: A Companion to Methods in Enzymology 15:283–294 and references cited therein). For comparison, an unmethylated DNA sample is isolated from cells grown without the inducer, or alternatively, transformed with a plasmid that does not contain the methyltransferase gene. That naked DNA is then modified with the methyltransferase(s) and S-adenosylmethionine in vitro to serve as a control for the context-dependence of modification by the enzyme.

Control and experimental DNA samples are then treated with sodium metabisulfite. Cytosine is deaminated to uracil while the methylated nucleotide remains relatively resistant to the modification. The DNA is purified and amplified by PCR, then subjected to sequence analysis (see Simpson, 1998, supra, and references cited therein for details; see also Examples 1–3). Since the rate of modification in a particular GpC sequence depends on the surrounding sequence, the comparison to be made is between the extent of modification in the chromatin sample with that of the naked DNA, in vitro-modified control.

The present invention is not limited to the analysis of DNA-protein interactions in Saccharomyces only. As discussed above, it is easily possible to adapt the methyltransferase of the invention for expression in whatever system is desired. For instance, but not limited to, one can use expression of the methyltransferase in Drosophila to study developmental effects of chromatin structure or position effect variegation. Similar experiments in maize can be informative in understanding biological variations in field crops. The use of the GpC-recognizing methyltransferase of the present invention will find broad utility in in situ analysis of chromatin structure and other DNA-protein interactions in a wide variety of organisms.

The in vivo chromatin structure mapping methodology facilitated by M.CviPI and other GpC-recognizing methyltransferases will also find utility in gene therapy. When a gene is transferred to a foreign cell for expression, expansion and eventual transfer to a patient to correct a genetic defect, the chromosomal context in which that gene integrates in the foreign cell is critical for its expression. The importance of chromosomal context for gene expression and the need for methods to achieve position independent, copy number dependent expression of transgenes have become increasingly apparent. Use of so-called insulator elements is one approach which may be combined with placing the gene of interest under influence of a locus control region, if such exists for the cell type in which expression is desired. Regardless of the strategy employed, it will be necessary to investigate chromatin organization around the transferred gene(s) in order to make a rational decision about the most appropriate mechanism of gene structure, transfer and expression. It is in this analysis and decision that the novel methyltransferase and the methodology described in the present invention is critical. This approach to chromatin structure analysis eliminates procedures which can lead to artifactual results resulting from invasive techniques, such as the use of DNA-cutting enzymes.

Another significant use of methyltransferases has been in development of cloning methodologies: the methyltransferase can modify nucleic acid bases so as to prevent their digestion by a particular restriction endonuclease and thereby allow cloning of much longer DNA fragments into particular vectors. This is important in creating cosmid, bacterial artificial chromosomes(BAC) and yeast artificial chromosome (YAC) clones which are critical to the sequencing of eucaryotic genomes. A limitation to this strategy is the frequency of restriction endonuclease sites where cutting must be abrogated and the absence of methyltransferases of appropriate specificity to block restriction enzyme activity. The novel methyltransferase enzyme of the present invention can help to overcome many of these difficulties. Singly or together with the other methyltransferases, such as M.SssI, the enzyme enables modification of many restriction sites to preclude their cutting during cloning procedures.

The novel methyltransferase and methodologies described herein may also be useful in the study and treatment of certain genetic diseases, some of which may occur due to abnormalities of chromatin organization that lead to inappropriate expression or repression of specific genes. Use of the methyltransferase and chromatin analysis methods of the invention to investigate chromatin organization of specific genes may prove beneficial in understanding such "chromatin diseases" and developing therapeutic approaches to their correction.

In addition to the above utilities for the M.CviPI gene and enzyme, this novel gene is scientifically significant in and of itself, inasmuch as it represents the first of a likely family of GpC dinucleotide cytosine methyltransferases. Accordingly, the nucleic acid molecules, proteins and antibodies of the present invention also may be used as research tools to explore the occurrence, expression and activity of GpC methyltransferases in Chlorella viruses and other organisms. For instance, M.CviPI nucleic acids may be used for a variety of purposes in accordance with the present invention. The DNA, RNA, or fragments thereof may be used as probes to detect the presence of and/or expression of M.CviPI genes. Methods in which M.CviPI nucleic acids may be utilized as probes for such assays include, but are not limited to: (1) in situ hybridization; (2) Southern hybridization (3) northern hybridization; and (4) assorted amplification reactions such as polymerase chain reactions (PCR).

The M.CviPI nucleic acids of the invention may also be utilized as probes to identify related genes from other species, including but not limited to, other viruses, plants, yeast, insects and mammals, including humans. As is well known in the art and described above, hybridization stringencies may be adjusted to allow hybridization of nucleic acid probes with complementary sequences of varying degrees of homology. Thus, M.CviPI nucleic acids may be used to advantage to identify and characterize other genes of varying degrees of relation to the exemplary coding sequence of SEQ ID NO:1, thereby enabling further characterization of this family of genes.

Purified M.CviPI proteins, or fragments thereof, may be used to produce polyclonal or monoclonal antibodies which also may serve as sensitive detection reagents for the presence and accumulation of M.CviPI protein in cultured cells or tissues and in intact organisms. Recombinant techniques enable expression of fusion proteins containing part or all of the M.CviPI protein. The full length protein or fragments of the protein may be used to advantage to generate an array of monoclonal or polyclonal antibodies specific for various epitopes of the protein, thereby providing even greater sensitivity for detection of the protein in cells or tissue.

Polyclonal or monoclonal antibodies immunologically specific for M.CviPI proteins may be used in a variety of assays designed to detect and quantitate the protein. Such assays include, but are not limited to: (1) flow cytometric analysis; (2) immunochemical localization in cultured cells or tissues; and (3) immunoblot analysis (e.g., dot blot, Western blot) of extracts from various cells and tissues.

Polyclonal or monoclonal antibodies that immunospecifically interact with the polypeptide encoded by M.CviPI can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

The following specific examples are provided to illustrate embodiments of the invention. They are not intended to limit the scope of the invention in any way.

EXAMPLE 1

Materials and Methods Used for Cloning and Characterizing the M.CviPI Gene and Analyzing Expression and Activity of the Encoded Enzyme Strains and plasmids. *Escherichia coli* strain DH5αmut10 (Dy, L., Chalasani, S. and Essani, K. (1993) *Gene*, 131, 87–91), lacking the mcrABC and mrr genes, and the vector pTZ18U were used for all the cloning and sequencing describe in Example 2 below. For expression of M.CviPI in *E.coli*, the DH5αmut10 lysogen of bacteriophage DE3 was constructed carrying the T7 RNA polymerase gene under control of the LacUV5 promoter (Studier, F. W., Rosenberg, A. H., Dunn, J. J. and Dubendorff, J. W. (1990) *Methods Enzymol.*, 185, 60–89). The plasmid pET20b+ is a T7 expression vector which adds a hexahistidine tag at the C-terminus of a cloned protein, while pLysS is a compatible plasmid providing a small amount of lysozyme (Novagen). The entire coding sequence of M.CviPI, with the SV40 nuclear localization signal appended at its N-terminus, was cloned into the yeast expression vector pMPK1 via the SfiI and SphI sites (Kladde, M. P., Xu, M. and Simpson, R. T. (1996) *EMBO J.*, 15, 6290–6300). The gene was subsequently integrated into the genomes of both YPH500ΔL (MATα ade2-101° his3-Δ200 leu2-Δ1 lys2-Δ1 trpl-Δ63 ura3-52) and YPH499ΔL (identical genotype but MATa) cells to create yeast strains MXY107 and MXY108, respectively (Kladde et al., 1996, supra) . These cell lines express the M.CviPI gene under the control of a GAL1 promoter.

PCR amplification of a fragment with high homology to conserved sequences of 5-$^{me}$C Mtases. Degenerate primers for PCR were MEC1 (5'-ccggatcCTNTTYGCNGGNAT-3') (SEQ ID NO:5), located in motif I, and MEC2 (5'-acctgcagRAANCCYTGRCANGGRAANCC-3') (SEQ ID NO:6), corresponding to motif IV of the conserved amino acid sequence of 5-$^{me}$C MTase. The sequence was chosen based on either the consensus sequence or, where there was no consensus, the sequence of M.CviJI (Shields, et al., 1990, supra; Posfai, J., Bhagwat, A. S., Posfai, G. and Roberts, R. J. (1989) *Nucleic Acids Res.*, 17, 2421–2435). Within the primer sequence, N represents a mixture of all four bases and lower case letters indicate sequence not existing in the MTase gene but introduced for the convenience of cloning (BamHI and PstI sites). Viral genomic DNA was amplified in 50 μl reactions which contained 40 pmol each primer, 10 pmol each DATP, dCTP, dGTP and dTTP, 1 μg DNA, 2.5 U Taq DNA polymerase (Fisher) in a buffer of 10 mM Tris-HCl (pH 8.3), 50 mM KCl, 3 mM $MgCl_2$, 0.05% (v/v) NP-40 and 0.05% (v/v) Tween 20. PCR cycling parameters were as follows:

preheating at 94° C. for 3 min; five cycles of 94° C. for 30 s, 42° C. for 30 s and 72° C. for 1 min; 20 cycles of 94° C. for 30 s, 60° C. for 30 s and 72° C. for 1 min. Reaction products were separated on a 1.5% agarose gel and fragments ~200–300 bp in size were purified from the gel, digested with BamHI and PstI, and subsequently cloned into pTZ18U. About 20 clones were sequenced and the DNA sequences of insertion fragments were translated into peptide sequences to compare with the amino acid sequence of M.CviJI.

Construction and screening of a Chlorella virus NYs-1 genomic library. A genomic library of Chlorella virus NYs-1 was constructed by partial digestion of viral DNA with Sau3AI, gel electrophoretic separation to enrich for fragments in the 2–4 kb size range and then ligation of the size-selected DNA fragments into BamHI-digested pTZ18U. The resultant plasmids were subsequently transformed into DH5αmut10 and clones with genomic DNA insertions were screened on plates containing X-Gal. The cloned, PCR-amplified fragment with homology to 5-$^{me}$C MTase was excised from the vector and random primer labeled in the presence of [$\alpha^{32}$P]DATP. About 1000–2000 colonies of the library were screened with this probe by in situ hybridization to obtain positive clones (Maas, R. (1983) *Plasmid*, 10, 296–301). Plasmid DNAs were purified from positive clones and the inserts sequenced to identify potential 5-$^{me}$C MTase genes.

Cell culture. Genes with high homology to known 5-$^{me}$C MTases were cloned in-frame in pET20b+ at the NdeI and EcoRI sites for expression in *E.coli*. The plasmid was then co-transformed into DH5αmut10 (DE3) with pLysS. Expression was induced as follows. Cells were grown to an OD$_{600}$ of ~0.4–0.6 and centrifuged prior to resuspension in fresh medium. IPTG was added to 0.4 mM for 2.5–4 h induction. Plasmids were then purified from induced cells and digested with a set of restriction enzymes (HindIII, HaeII, HaeIII, HhaI and AvaII) to detect the presence of MTase activity. For the expression of 5-$^{me}$C MTases in yeast, a starter culture was grown overnight at 30° C. in YPG medium (10 g yeast extract, 20 g peptone, 20 g galactose/l) to an OD$_{600}$ of ~1. Cells were centrifuged and resuspended in fresh YPG medium for growth at 30° C. for an additional 16 h. DNA from ~3 ml cells was rapidly isolated by the glass bead method for deamination as described below (Rose, M. D., Winston, F. and Hieter, P. (1990) *Methods in Yeast Genetics: A Laboratory Course Manual*. Cold Spring Harbor Laboratory Press, Cold Spring Harbor, N.Y.).

Determination of methylation specificity of M.CviPI in *E.coli* and yeast. The DNA sequence recognized by M.CviPI was investigated by bisulfite genomic sequencing. Either linearized plasmid (pET20b+ or pET-NYs-1-5) DNA purified from *E.coli* cells or genomic DNA purified from yeast cells was treated by the method initially developed by Frommer et al. (1992, supra) and further modified by Kladde et al. (1996, supra) . Briefly, DNA is subjected to quantitative deamination with sodium metabisulfite, converting all deoxycytidine residues to deoxyuridine, while 5-$^{me}$C residues, created by the MTase in vivo, resist deamination. Subsequent PCR amplification of selected DNA regions yields a product that is directly sequenced to provide a positive display of 5-$^{me}$C. The primers used for the *E.coli* pET20b+ plasmid were as follows: pair I (FIG. 1A): CCdeamin1a, 5'-CCATTCAACCCAACCACTACAC-3' (SEQ ID NO:7; the primer for sequencing), and CCdeamin1b, 5'-GGGTTTTGTGGTATTATTGTAGTATT GG-3' (SEQ ID NO:8); pair II (FIG. 1B): PET3336, 5'-TACCTAACTCCCCATCATATAAATAACTACA-3' (SEQ ID NO:9), and PET3849, 5'-TTTTTAGAATGATTTG GTTGAGTATTTATTAG-3' (SEQ ID NO:10). The primers for the yeast STE6 gene were as follows: STE6a1a, 5'-CTAATTATAATTCACAAATACACCTCAAAAA-3' (SEQ ID NO:11; the primer for sequencing, from 45331 to 45361 m.u. of chromosome XI), and STE6a2a, 5'-AAGTTAGGTTATTTTTGATGGTTTTATTG-3' (SEQ ID NO:12; from 45871 to 45843 m.u. of chromosome XI). After PCR amplification, products were analyzed directly by thermal cycle sequencing as described previously (Kladde et al., 1996, supra).

Enzyme purification and MTase assay. All *E.coli* culture was induced as described above for enzyme purification. Cells were sonicated in 10 ml binding buffer (5 mM imidazole, 0.5 M NaCl and 20 mM Tris-HCl, pH 7.9). Cell debris was removed by centrifugation (20 min at 10 000 g) and the supernatant was applied to a Ni$^{2+}$-agarose column (1×1 cm). Following sequential washes with 10 ml binding buffer,10 ml wash buffer I (60 mM imidazole, 0.5 M NaCl and 20 mM Tris-HCl, pH 7.9) and 1.5 ml wash buffer II (100 mM imidazole, 0.5 M NaCl and 20 mM Tris-HCl, pH 7.9), the bound enzyme was eluted with 1.5 ml elution buffer (500 mM imidazole, 0.5 M NaCl and 20 mM Tris-HCl, pH 7.9). The eluate was applied to a phosphocellulose column (Whatman P11, 1×1 cm) equilibrated with 20 mM Tris (pH 8.0), 50 mM NaCl and 1 mM EDTA. Protein was eluted stepwise with 2 ml portions of the same buffer containing NaCl from 0.1 to 1.0 M in 0.1 M increments. Fractions of 0.5 ml were collected and the fractions (0.3–0.4 M NaCl) containing the predicted 41 kDa protein band were pooled and concentrated using a Centricon concentrator (Amicon). The final enzyme solution was kept at −80° C. in a buffer of 20 mM Tris (pH 8.0), 1 mM EDTA, 2 mM DTT and 10% (v/v) glycerol.

Cytosine MTase activity was assayed in a 20 μl reaction containing 20 mM Tris (pH 8.0), 1 mM EDTA, 2 mM DTT, 0.32 nM S-adenosyl methionine (New England Biolabs), 1 μg pTZ18U plasmid DNA and 1 μl enzyme fraction. After incubation for 1 h at 37° C., the reaction was stopped by extraction with StrataClean resin (Stratagene). Following ethanol precipitation, the DNA was digested with HaeIII and analyzed on 1% agarose gels. HaeIII cleaves GGCC but not GG$^{me}$CC sequences (Mann, M. B. and Smith, H. O. (1977) *Nucleic Acids Res* 4, 4211–4221; Backman,K. (1980) *Gene*, 11, 169–171). Therefore, lack of HaeIII cleavage implies a MTase which methylates the internal cytosine in GGCC sites.

EXAMPLE 2

Cloning and Characterization of M.CviPI Gene from Chlorella Virus NYs-1

Using the methods set forth in Example 1, a new dinucleotide 5-$^{me}$C MTase gene, called M.CviPI, was cloned from Chlorella virus NYs-1. We used the high conservation at motifs I and IV to design primers for PCR amplification of a fragment spanning these two regions. This PCR fragment was then used to probe an NYs-1 genomic library to finally clone the M.CviPI gene.

Isolation and identification of the M.CviPI gene from Chlorella virus Nys-1. The Chlorella virus NYs-1 genome contains a very high level of 5-$^{me}$C (47.5%) (Schuster, A. M., Burbank, D. E., Meister, B., Skrdla, M. P., Meints, R. H., Hattman, S., Swinton, D. and Van Etten, J. L. (1986) *Virology*, 150, 170–177). The resistance/sensitivity of its DNA to >70 methylation-sensitive restriction endonucleases indicated that the virus probably encodes several 5-$^{me}$C MTases (Nelson & Van Etten, 1993, supra, Nelson et al., 1998, supra) . Sequence alignment of M.CviJI, the only cytosine MTase cloned from a Chlorella virus, with the conserved motifs of other 5-$^{me}$C MTases indicated that the two most conserved motifs of M.CviJI are motif I and motif IV. These motifs, which are usually ~200 bp apart (Posfai et al., 1989, supra), correspond to the Ado-Met binding site and the catalytic site in the crystal structure of the HhaI and HaeIII MTases (Cheng, X., Kumar, S., Posfai, J., Pflugrath, J. W. and Roberts, R. J. (1993) *Cell*, 74, 299–307; Reinisch, K. M., Chen, L., Verdine, G. L. and Lipscomb, W. N. (1995) *Cell*, 82, 143–153). A pair of degenerate primers based on the consensus amino acid sequence within the two motifs was used for PCR with NYs-1 DNA. These primers generated several bands ranging from 150 bp to 2 kb, with a prominent band around 200 bp (data not shown). The ~200 bp fragment was gel purified and cloned into pTZ18U following digestion with PstI and BamHI. Sequence analysis of ~20 different transformants identified six different fragments, each of which encoded part of an ORF with high homology to M.CviJI as well as other 5-$^{me}$C MTases. Southern blotting with NYs-1 genomic DNA using each of the six fragments as the probe confirmed that these sequences do occur in the viral genome.

To clone the full-length gene of the putative 5-$^{me}$C MTases, a genomic library of NYs-1 was constructed in pTZ18U, a non-expressing vector, to avoid possible toxicity resulting from a high level of methylation. One of the six cloned PCR fragments was used as a hybridization probe to isolate six positive clones which contained a viral genomic fragment with homology to the probe. Sequence analysis of each of the positive clones revealed that two of them contained a fragment encoding the same, full-length ORF with high homology to 5-$^{me}$C MTases.

To further characterize this potential MTase gene, the coding sequences were fused to a His$_6$ tag within the expression vector pTZ20b+, cloned into strain DH5αmut10 (DE3) and tested for expression (Materials and Methods). One of the clones, designated pETNYs-1-5, expressed a MTase activity which resulted in plasmid DNA that was resistant to digestion by HhaI, HaeII and HaeIII (data not shown). NYs-1 viral DNA is also resistant to these same enzymes (data not shown).

The methylation specificity of clone pETNYs-1-5 was examined by bisulfite genomic sequencing. Briefly, pETNYs-1-5 purified from induced cells was deaminated and, following PCR amplification, its methylation pattern was determined by thermal cycle sequencing (FIG. 1). pETNYs-1-5 DNA was methylated at all GpC sites within the resolvable sequences under investigation, suggesting that the plasmid contains a gene encoding a MTase recognizing GpC sites. The pET20b+ vector purified from the same *E.coli* strain grown under the same induction conditions was devoid of methylation. Thus, the MTase activity is encoded by the viral genomic fragment inserted into the vector; the gene was named M.CviPI. In addition, the sequences investigated in FIG. 1A and 1B include all GpC sites with all 16 possible combinations of flanking bases. Each of these sites was methylated, identifying the enzyme as a cytosine MTase recognizing just the dinucleotide GpC irrespective of flanking sequence context.

Sequence comparison of M.CviPI and other 5-$^{me}$C Mtases. The amino acid sequence comparison of M.CviPI with the sequences of other 5-$^{me}$C MTases supports its identification as a 5-$^{me}$C MTase. Sequence alignment was performed for M.CviPI (GenBank accession no. AF062394), M.CviJI (GenBank accession no. P36216) and M.HaeIII (GenBank accession no. AAC05696), a bacterial MTase recognizing GpGpCpC sequences. The three enzymes have the dinucleotide GpC as the whole or a part of their recognition sequence. As shown in FIG. 2, significant conservation exists for the sequences of all three proteins, although conservation between the enzymes from the two Chlorella viruses (66% amino acid identity) is higher than for either of these with the bacterial enzyme (~20% amino acid identity). In terms of the six most highly conserved motifs identified in other 5-$^{me}$C MTases (Posfai et al., 1989, supra), high conservation of motifs I and IV occurs for all three proteins. Motifs VI and VIII can be identified in all three, albeit with a lesser extent of amino acid conservation. No apparent conservation of motifs IX and X exists. According to the crystal structures of both M.HhaI and M.HaeIII (Cheng et al., 1993, supra; Reinisch et al., 1995, supra), motif I belongs to the structural segment that forms part of the Ado-Met binding site and motif IV contains the key catalytic cysteinyl residue. These two motifs are directly responsible for the methylation reaction. Motifs VI and VIII are also located around the active site and several interactions occur between them and the Pro-Cys catalytic region (Cheng et al., 1993, supra; Reinisch et al., 1995, supra). In general, these four motifs comprise most of the structures that surround the active site cleft. In addition, Gln188 of M.CviJI, which when mutated leads to an inactive pseudogene in Chlorella virus, is conserved in M.CviPI (Zhang, Y., Nelson, M. and Van Etten, J. L. (1992) *Nucleic Acids Res*, 20, 1637–1642). Motifs IX and X, on the other hand, are more likely to be involved in forming a structural framework for the functional domains. In motif X, the only real conservation includes several hydrophobic side chains involved in packing against α-helix A, an important component of the core structure of the protein. Motif IX has extensive interactions with the variable region and, therefore, may well be involved in sequence-specific recognition of DNA, a feature which should be variable among different 5-$^{me}$C MTases. In fact, M.HaeIII interacts with its cognate DNA in a different way than does M.HhaI (Reinisch et al., 1995, supra), consistent with the lack of significant sequence conservation between the two enzymes in this region. Both M.CviPI and M.CviJI were isolated from Chlorella viruses and are predicted to be very distant in evolutionary time from bacterial 5-$^{me}$C MTases. Given the evolutionary differences as well as different target sequences, it is not surprising to find high sequence conservation in the regions involved directly in the mechanisms of cofactor binding and catalysis, with less sequence conservation in the other regions.

The high amino acid conservation between M.CviPI and M.CviJI, cytosine MTases isolated from two different viruses, NYs-1 and IL-3A, and their common GpC methylation sites is quite interesting in the context of mechanisms leading to the profusion of restriction/modification systems in Chlorella viruses. It will be interesting if additional enzymes can be isolated from some of the Chlorella viruses which recognize versions of GpC or RGC(T/C/G) sites. The high level of sequence conservation reinforces the possibility of cloning such additional 5-$^{me}$C MTases from Chlorella viruses by the sequence homology strategy.

EXAMPLE 3

Expression and Activity of M.CviPI In *E. coli* and *S. cerevisiae*

This example describes the expression of the M.CviPI gene in bacteria. The expressed protein was purified and demonstrated to methylate GpC in vitro. The M.CviPI gene was also successfully expressed in yeast to produce an active protein, indicating that the enzyme can be used to increase the resolution of in vivo chromatin mapping.

Purification of M.CviPI protein. The pET20b+ plasmid, containing the M.CviPI gene, was introduced into E.coli strain DH5αmut10 (DE3) for expression. Lack of the mcrABC and mrr genes in this bacterial strain should decrease any possible toxicity of high levels of cytosine methylation (Raleigh, E. A. (1987) Methods Enzymol., 152, 130–141). To further reduce the chance of possible deleterious effects of M.CviPI expression, another compatible plasmid, pLysS, was transformed into the same host. pLysS contains a gene encoding lysozyme, which is an inhibitor of T7 RNA polymerase (Studier et al., 1990, supra). The low level of lysozyme produced from the plasmid inhibits any T7 RNA polymerase activity resulting from leaky repression of the LacUV5 promoter and thereby allows more stringent control of MTase production.

Induction of cells at an $OD_{600}$ of ~0.4–0.6 for 2.5–4 h with 0.4 mM IPTG led to an increase in a protein of 41 kDa, the predicted size of M.CviPI protein (FIG. 3A). The majority of the induced protein was insoluble. Following purification of the soluble enzyme by $Ni^{2+}$-agarose and phosphocellulose column chromatography, a dominant single band was observed on SDS gel electrophoresis after Coomassie blue staining (FIG. 3A). A semi-quantitative but highly specific MTase activity assay was performed after each step of purification. The assay measures selectively only those $5-^{me}C$ MTases which modify the internal cytosine in a GpGpCpC context and thereby make DNA resistant to digestion by the HaeIII restriction endonuclease (Mann & Smith, 1977, supra; Backman, 1980, supra). Throughout the purification, enzyme activity paralleled the presence of the 41 kDa protein band, consistent with its identity as the $5-^{me}C$ MTase M.CviPI. The purified enzyme after the final phosphocellulose column chromatography step exhibited an Ado-Met-dependent MTase activity (FIG. 3B). While we cannot compare a specific activity of the purified M.CviPI with other methyltransferases, the isolated M.CviPI enzyme shows specificity that is unique. It also lacks contaminating nucleic acid degrading or modifying activities that would impair its use in control of restriction endonuclease activity in cloning or in chromatin structure mapping.

Expression of M.CviPI in yeast shows its potential for chromatin mapping. The M.CviPI gene was cloned and expressed in S.cerevisae, a eukaryotic organism lacking endogenous methylation of DNA, enabling unambiguous detection of de novo modification. Expression of the protein in yeast was under control of the GALL promoter, a strong yeast promoter tightly regulated by carbon source, that is repressed in glucose and induced in galactose (Johnston, M., Flick, J. S. and Pexton, T. (1994) Mol. Cell. Biol., 14, 3834–3841). Transfection of the cloned gene together with its controllable promoter into the genomic LYS2 locus created a single copy, stable integrant similar to that used in our previous studies of DNA methylation and chromatin structure in S.cerevisiae (Kladde et al., 1996, supra) . A region located near the 3'-end of the coding sequence of STE6 was chosen for bisulfite genomic sequencing, as it is known to be devoid of positioned nucleosomes which may obscure determination of the methyltransferase specificity. After induction by growing yeast cells in medium containing galactose, genomic DNA was purified and deaminated to determine the methylation pattern, as previously described (Kladde et al., 1996, supra) . As shown in FIG. 4, M.CviPI recognizes and methylates GpC in yeast, just as it does in E.coli. Within the sequence resolvable on the gel, M.CviPI methylated every GpC site. Like other MTases (Kladde et al., 1996, supra), the extent of modification of individual, specific sites is context dependent. In spite of variability in the modification level, studies of several regions of yeast genomic DNA demonstrated that the M.CviPI enzyme can methylate cytosine in any GpC context, independent of the flanking nucleotide sequences. Successful expression of M.CviPI in yeast confirms its potential for in vivo chromatin mapping studies. In addition, the fact that the GpC dinucleotide is slightly over-represented in the yeast genome increases the resolution of chromatin mapping using M.CviPI. Within chromosomes I, III, IV and XI, comprising 17% of the total yeast genome, there is one GpC site every 27.9 bp, as compared with one CpG site every 35.7 bp. Thus, in combination, M.CviPI and M.SssI lead to a resolution of one naturally occurring site every 15.6 bp in chromatin mapping in S.cerevisiae (Dujon et al., 1994, supra; Bussey, H., Kaback, D. B., Zhong, W., Vo, D. T., Clark, M. W., Fortin, N., Hall, J., Ouellette, B. F., Keng, T., Barton, A. B. et al). (1995) Proc. Natl Acad. Sci. USA, 92, 3809–3813; Jacq, C., Alt-Morbe, J., Andre, B., Arnold, W., Bahr, A., Ballesta, J. P., Bargues, M., Baron, L., Becker, A., Biteau, N. et al) . (1997) Nature, 387 (suppl. 6632), 75–78).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. An isolated nucleic acid molecule comprising the polynucleotide of SEQ ID NO:1.

2. A vector for transforming cells comprising the isolated nucleic acid molecule of claim 1.

3. Cells transformed with the vector of claim 2.

4. The cells of claim 3, originating from a source selected from the group consisting of bacteria, yeast, fungi, insects, plants and mammals.

5. A cultured cell line of the transformed cells of claim 4.

6. An oligonucleotide between about 10 and 100 nucleotides in length that, under predetermined conditions, hybridizes with a portion of the isolated nucleic acid molecule of claim 1, wherein the predetermined conditions comprise hybridizing in 5×SSC, 5×Denhardt's reagent, 1% SDS, 100 µg/ml denatured, fragmented salmon sperm DNA, 0.05% sodium pyrophosphate, and 50% formamide at 42° C. and following hybridization, filters are washed as follows:
    (1) 5 minutes at room temperature in 2×SSC and 1% SDS;
    (2) 15 minutes at room temperature in 2×SSC and 0.1% SDS; (3) 30 minutes-1 hour at 37° C. in 2×SSC and 0.1% SDS; (4) 2 hours at 45–55° C. in 2×SSC and 0.1% SDS, changing the solution every 30 minutes.

7. An isolated nucleic acid molecule comprising a polynucleotide that, under predetermined conditions, hybridizes with the polynucleotide of SEQ ID NO:1, wherein the predetermined conditions comprise hybridizing in 5×SSC, 5×Denhardt's reagent, 1% SDS, 100 µg/ml denatured, fragmented salmon sperm DNA, 0.05% sodium pyrophosphate, and 50% formamide at 42° C. and following hybridization, filters are washed as follows:
    (1) 5 minutes at room temperature in 2×SSC and 1% SDS;
    (2) 15 minutes at room temperature in 2×SSC and 0.1% SDS; (3) 30 minutes-1 hour at 37° C. in 2×SSC and 0.1% SDS; (4) 2 hours at 45–55° C. in 2×SSC and 0.1% SDS, changing the solution every 30 minutes.

8. A vector for transforming cells comprising the isolated nucleic acid molecule of claim 7.

9. Cells transformed with the vector of claim 8.

10. The cells of claim 9, originating from a source selected from the group consisting of bacteria, yeast, fungi, insects, plants and mammals.

11. A cultured cell line of the transformed cells of claim 10.

12. An isolated nucleic acid molecule comprising a polynucleotide encoding the polypeptide of SEQ ID NO:2.

13. A recombinant DNA molecule comprising the isolated nucleic acid molecule of claim 12, wherein the recombinant DNA molecule is operably inserted into a vector for transforming cells.

14. Cells transformed with the recombinant DNA molecule of claim 13.

15. The cells of claim 14, originating from a source selected from the group consisting of bacteria, yeast, fungi, insects, plants and mammals.

16. A cultured cell line of the transformed cells of claim 15.

* * * * *